(12) United States Patent
McKenna et al.

(10) Patent No.: US 11,541,278 B2
(45) Date of Patent: Jan. 3, 2023

(54) METHODS AND APPARATUS FOR MANAGING SEQUENTIAL TASKS VIA TASK SPECIFIC USER INTERFACE ELEMENTS

(71) Applicant: MYFITNESSPAL, INC., San Francisco, CA (US)

(72) Inventors: Lauren McKenna, Austin, TX (US); Gloria Wu, Austin, TX (US); Scott Laing, Austin, TX (US)

(73) Assignee: MyFitnessPal, Inc., San Francisco, CA (US)

( * ) Notice: Subject to any disclaimer, the term of this patent is extended or adjusted under 35 U.S.C. 154(b) by 228 days.

(21) Appl. No.: 16/848,059

(22) Filed: Apr. 14, 2020

(65) Prior Publication Data

US 2021/0316185 A1     Oct. 14, 2021

(51) Int. Cl.
| | |
|---|---|
| *G06F 3/048* | (2013.01) |
| *A63B 24/00* | (2006.01) |
| *G06F 3/0482* | (2013.01) |
| *A63B 71/06* | (2006.01) |
| *H04L 67/50* | (2022.01) |

(52) U.S. Cl.
CPC ...... *A63B 24/0062* (2013.01); *A63B 71/0619* (2013.01); *G06F 3/0482* (2013.01); *A63B 2024/0068* (2013.01); *A63B 2071/0675* (2013.01); *A63B 2220/17* (2013.01); *A63B 2225/20* (2013.01); *H04L 67/535* (2022.05)

(58) Field of Classification Search
CPC ............ A63B 24/0062; A63B 71/0619; A63B 2024/0068; A63B 2071/0675; A63B 2220/17; A63B 2225/20; G06F 3/0482; H04L 67/22
See application file for complete search history.

(56) References Cited

U.S. PATENT DOCUMENTS

| | | | |
|---|---|---|---|
| 10,777,314 B1 * | 9/2020 | Williams | A61B 5/1118 |
| 11,107,569 B1 * | 8/2021 | Devoto | G16H 40/67 |
| 11,161,010 B2 * | 11/2021 | Williams | A63B 24/0084 |
| 11,216,119 B2 * | 1/2022 | De Vries | G06F 3/0485 |
| 2017/0143262 A1 * | 5/2017 | Kurunmäki | A61B 5/72 |
| 2018/0126248 A1 * | 5/2018 | Dion | A63B 23/1227 |
| 2019/0214125 A1 * | 7/2019 | Zeller | G16H 50/30 |

(Continued)

*Primary Examiner* — David Phantana-angkool
(74) *Attorney, Agent, or Firm* — Maginot, Moore & Beck, LLP

(57) ABSTRACT

Systems, apparatus, and methods for managing workouts via exercise specific user interface elements. Various embodiments of the present disclosure are directed to exercise specific user interface elements (e.g., floating smart timers, etc.) that are automatically pre-populated with data based on prescribed workout information. The user is provided a workout that includes a number of different exercises, and their prescribed completion values. The user can perform the workout and quickly log the pre-populated completion values (if accurate), or alternatively manually enter actual workout data. Additionally, the user can quickly transition through their "checklist" of exercises, based on the prescribed ordering of the workout. The resulting workout data record can be automatically logged at the end of the workout session. The exercise specific user interface allows a user to log workout activity with minimal distraction.

20 Claims, 8 Drawing Sheets

(56) References Cited

U.S. PATENT DOCUMENTS

| | | | |
|---|---|---|---|
| 2020/0054931 A1* | 2/2020 | Martin | A61B 5/486 |
| 2020/0179757 A1* | 6/2020 | Toivonen | G16H 10/20 |
| 2021/0146195 A1* | 5/2021 | Szpiczynski | G16H 40/67 |
| 2021/0153805 A1* | 5/2021 | Carpenter | A61B 5/681 |
| 2021/0154530 A1* | 5/2021 | Carpenter | A63B 24/0075 |
| 2021/0255826 A1* | 8/2021 | Devine | G06F 3/04817 |
| 2021/0316185 A1* | 10/2021 | McKenna | G16H 40/67 |
| 2022/0016480 A1* | 1/2022 | Bissonnette | G06N 20/20 |
| 2022/0023718 A1* | 1/2022 | Augustin | G06F 3/04815 |
| 2022/0047921 A1* | 2/2022 | Bissonnette | A63B 23/0417 |
| 2022/0093230 A1* | 3/2022 | Gupta | A63B 24/0084 |
| 2022/0176201 A1* | 6/2022 | Wehba | G06T 7/20 |
| 2022/0258005 A1* | 8/2022 | Kashyap | A63B 71/0622 |
| 2022/0272507 A1* | 8/2022 | Park | H04W 4/40 |

\* cited by examiner

METHODS AND APPARATUS FOR MANAGING SEQUENTIAL TASKS VIA TASK SPECIFIC USER INTERFACE ELEMENTS

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

TECHNICAL FIELD

This disclosure relates generally to the field of user interfaces. More particularly, the present disclosure relates to systems, computer programs, devices, and methods for managing and recording sequential activities.

DESCRIPTION OF RELATED TECHNOLOGY

In recent years, health and fitness tracking applications that track user workouts and activities have become very popular. Routine physical activity is important to a healthy lifestyle and is known to prevent and/or ameliorate various health conditions, such as diabetes and obesity. Health and fitness tracking applications allow users to set and achieve personalized health goals by tracking the user's physical activity, regularity of physical activity, and/or intensity of physical activity.

Fitness tracking applications are typically used in fitness settings where the user's attention is focused on physical exertion (e.g., not the fitness tracking application). Managing and recording workout activity under these situations can be difficult.

SUMMARY

The present disclosure addresses the foregoing needs by disclosing, inter alia, methods, devices, systems, and computer programs for managing sequential tasks via task specific user interface elements, thereby enabling a user to focus on the task at hand rather than recording their activity.

In one aspect, a user apparatus is disclosed. In one embodiment, the user apparatus includes: a user interface; a network interface; a processor; and a non-transitory computer-readable medium including one or more instructions. In one exemplary embodiment, the one or more instructions, when executed by the processor, causes the user apparatus to: obtain a workout including a plurality of exercises, wherein at least one exercise of the plurality of exercises includes a prescribed completion value; for the at least one exercise of the plurality of exercises: display an exercise specific user interface element based on the prescribed completion value; log an actual completion value; and transmit the actual completion value to a fitness server.

In one variant, the prescribed completion value includes a duration; and the exercise specific user interface element includes a timer set to the duration.

In one variant, the prescribed completion value includes a number of repetitions; and the exercise specific user interface element includes a counter set to the number of repetitions.

In one variant, the prescribed completion value includes a distance; and the exercise specific user interface element includes a distance tracker set to the distance.

In one variant, another exercise of the plurality of exercises includes another prescribed completion value; and the one or more instructions, when executed by the processor, causes the user apparatus to display another exercise specific user interface element based on the another prescribed completion value.

In one variant, the exercise specific user interface element causes the prescribed completion value to be logged as the actual completion value.

In one variant, the user apparatus further includes a sensor; and the one or more instructions, when executed by the processor, causes the user apparatus to sense the actual completion value.

In one aspect, a user apparatus is disclosed. In one embodiment, the user apparatus includes: a user interface; a network interface; a processor; and a non-transitory computer-readable medium including one or more instructions. In one embodiment, the one or more instructions when executed by the processor, causes the user apparatus to: obtain a workout including a plurality of exercises, wherein the plurality of exercises has a prescribed sequence; for at least one exercise of the plurality of exercises: display a first exercise specific user interface element for the at least one exercise; and responsive to completion of the at least one exercise, transition to a next exercise of the workout based on the prescribed sequence; and transmit a completion value for the at least one exercise to a fitness server.

In one variant, the one or more instructions, when executed by the processor, causes the user apparatus to display a second exercise specific user interface element for the next exercise of the workout, where the first exercise specific user interface element differs from the second exercise specific user interface element.

In one variant, the workout further includes at least one alternate exercise. In one such variant, the one or more instructions, when executed by the processor, causes the user apparatus to: responsive to a user input, transition to the at least one alternate exercise.

In one variant, the workout further includes an alternate plurality of exercises. In one such variant, the one or more instructions, when executed by the processor, causes the user apparatus to transition to the alternate plurality of exercises based on the completion value for the at least one exercise.

In one variant, the one or more instructions, when executed by the processor, causes the user apparatus to: responsive to a user input, modify the prescribed sequence.

In one aspect, a method for controlling a workout and logging of exercise metrics is disclosed. In one embodiment, the method includes: obtaining the workout including an exercise; displaying an exercise specific user interface element based on a prescribed value associated with the exercise; logging an actual completion metric for the exercise; and providing the actual completion metric to a fitness server.

In one variant, the prescribed value includes a modality of exercise measurement.

In one variant, the prescribed value includes a prescribed sequence.

In one variant, the prescribed value includes a prescribed completion value. In one such variant, the method further includes pre-populating the exercise specific user interface element based on the prescribed completion value. In another variant, the method further includes logging the prescribed completion value as the actual completion metric.

More generally, various aspects of the present disclosure are directed to systems, apparatus, methods and storage media which enable sequential task management and logging in environments where the user is focused on the task at hand, rather than the user interface. Specifically, the described system and method enables users to focus on their physical exertion rather than user interface navigation.

Other features and advantages of the present disclosure will immediately be recognized by persons of ordinary skill in the art with reference to the attached drawings and detailed description of exemplary embodiments as given below.

Figure 1A:
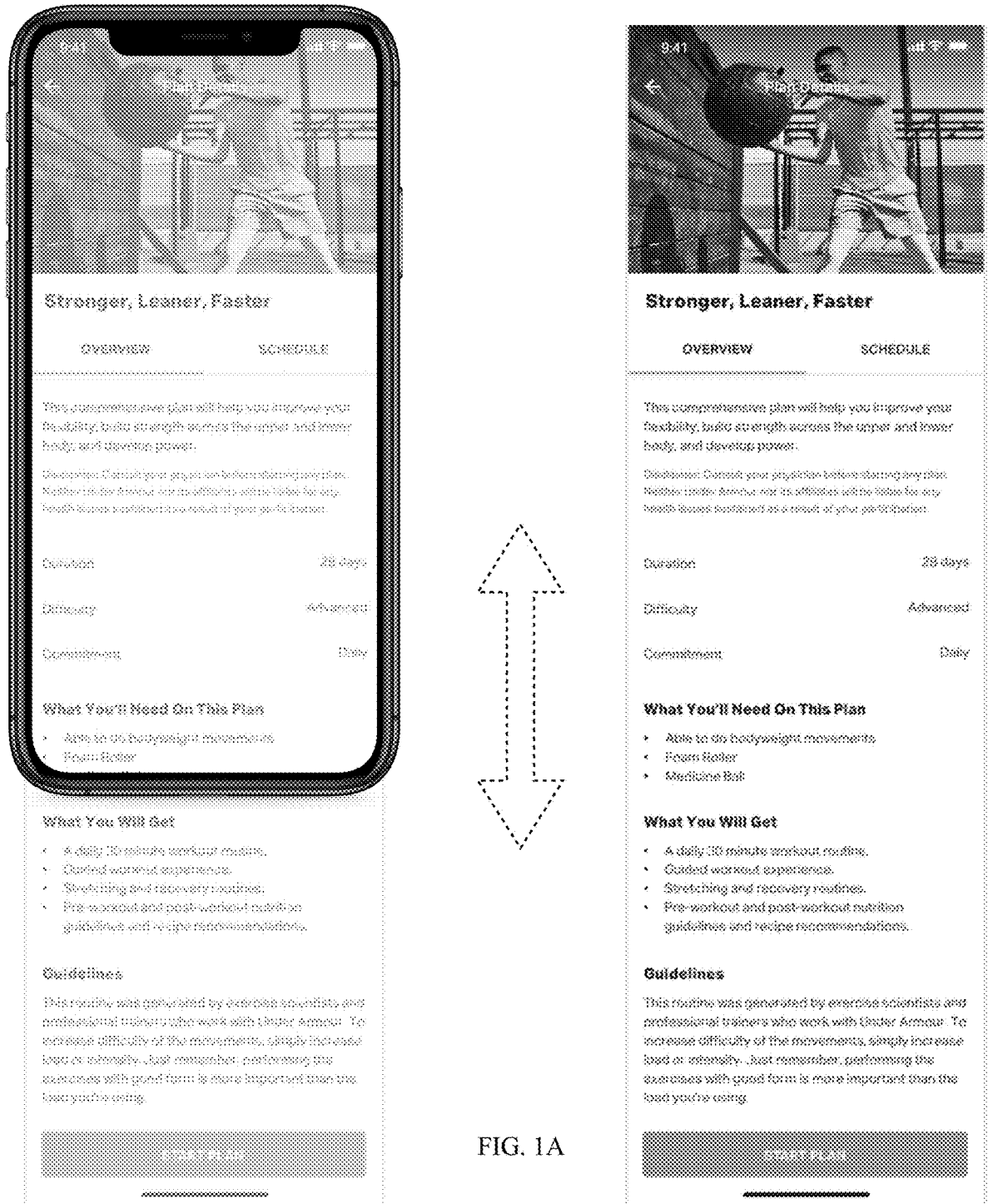
FIG. 1A is a graphical representation of an exemplary training plan summary, useful for describing various aspects of the present disclosure.

All Figures ©Under Armour, Inc, 2019-2020. All rights reserved.

DETAILED DESCRIPTION

Disclosed embodiments include systems, apparatus, methods and storage media which manage sequential tasks via task specific user interfaces.

In the following detailed description, reference is made to the accompanying drawings which form a part hereof wherein like numerals designate like parts throughout, and in which is shown, by way of illustration, embodiments that may be practiced. It is to be understood that other embodiments may be utilized, and structural or logical changes may be made without departing from the scope of the present disclosure. Therefore, the following detailed description is not to be taken in a limiting sense, and the scope of embodiments is defined by the appended claims and their equivalents.

Aspects of the disclosure are disclosed in the accompanying description. Alternate embodiments of the present disclosure and their equivalents may be devised without departing from the spirit or scope of the present disclosure. It should be noted that any discussion herein regarding "one embodiment", "an embodiment", "an exemplary embodiment", and the like indicate that the embodiment described may include a particular feature, structure, or characteristic, and that such particular feature, structure, or characteristic may not necessarily be included in every embodiment. In addition, references to the foregoing do not necessarily include a reference to the same embodiment. Finally, irrespective of whether it is explicitly described, one of ordinary skill in the art would readily appreciate that each of the particular features, structures, or characteristics of the given embodiments may be utilized in connection or combination with those of any other embodiment discussed herein.

Various operations may be described as multiple discrete actions or operations in turn, in a manner that is most helpful in understanding the claimed subject matter. However, the order of description should not be construed as to imply that these operations are necessarily order dependent. In particular, these operations may not be performed in the order of presentation. Operations described may be performed in a different order than the described embodiment. Various additional operations may be performed and/or described operations may be omitted in additional embodiments.

For the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B and C). Similar logic applies to the use of the term "or" herein; i.e., "A or B" means (A), (B), or (A and B).

The terms "comprising," "including," "having," and the like, as used with respect to embodiments of the present disclosure, are synonymous.

Personalized Training and Fitness Tracking Devices

Human personal trainers can improve workout efficacy by monitoring performance and prescribing exercises in real-time. Additionally, personal trainers can focus the exerciser's attention and provide motivation when needed. Historically, personalized training results in faster performance progression (e.g., reduced injury/recovery and better outcomes.) Unfortunately, hiring a personal trainer can be cost-prohibitive for most gym goers.

Modern consumer electronics have the potential to provide the benefits of personalized training to broad segments of the exercising public, however many challenges exist. Popular workout protocols often mix different exercises; in some such cases, workouts may require e.g., high intensity exercises, performed in rapid succession, and require different types of exercise measurement modalities. For example, high intensity workouts may combine distance-based exercises (e.g., run 1 mile for time, sprint 100 yards, etc.), repetition-based exercises (e.g., 20 push-ups, 10 pull-ups, 30 squats, etc.), and/or time-based exercises (1 minute of jump rope, 20 box jumps as fast as you can, etc.)

Unfortunately, existing fitness tracking applications rely on user interface components that require the user's full attention to operate (e.g., a touchscreen, menu navigation, scroll bars, etc.) This can be particularly problematic when a user is trying to concentrate on their workout. For example, starting and stopping location tracking, and/or setting a countdown timer/stopwatch can require time and attention that may disrupt a high intensity workout. Additionally, capacitive touchscreen granularity can be heavily affected by foreign substances (such as sweat, saliva, and chalk) on fingertips. Attempting to perform fine detail manipulations via a capacitive touchscreen mid-workout can be frustratingly inaccurate (e.g., keyboard based numeric input of repetitions, navigating through a list to find the next exercise in the workout, etc.)

Additionally, modern fitness tracking applications can provide users with a virtually limitless library of workouts and/or exercises. However, the abundance of exercise options could overwhelm and detract from a user's fitness tracking experience. Fitness tracking applications enable workout logging and access to workout history from virtually anywhere, but manual data entry is tedious and time consuming. In some cases, users may also vary widely in their reporting consistency (one workout may be meticulously logged, whereas another workout may be replete with data entry errors). This can be particularly exacerbated when a user has a long list of exercises to track; logging mid-workout can disrupt intensity, and logging after completion is heavily reliant on a user's memory.

More directly, existing fitness tracking applications require too much attention to operate. New solutions for prescribing workouts, seamlessly monitoring performance, and recording actual exercise history, are needed. Ideally, such solutions should operate in real-time, in fitness settings, with minimal user distraction.

Example Operation

In one exemplary embodiment, a user completes an initial "onboarding" program that identifies a user specific training plan. As but one such example, the onboarding process may suggest several possible training plans; the user selects a training plan that best matches their personal fitness goals. FIG. 1A is a graphical representation of one such training plan. The selected training plan is stored within the health and fitness network and/or within the user's personal devices.

Figure 1B:
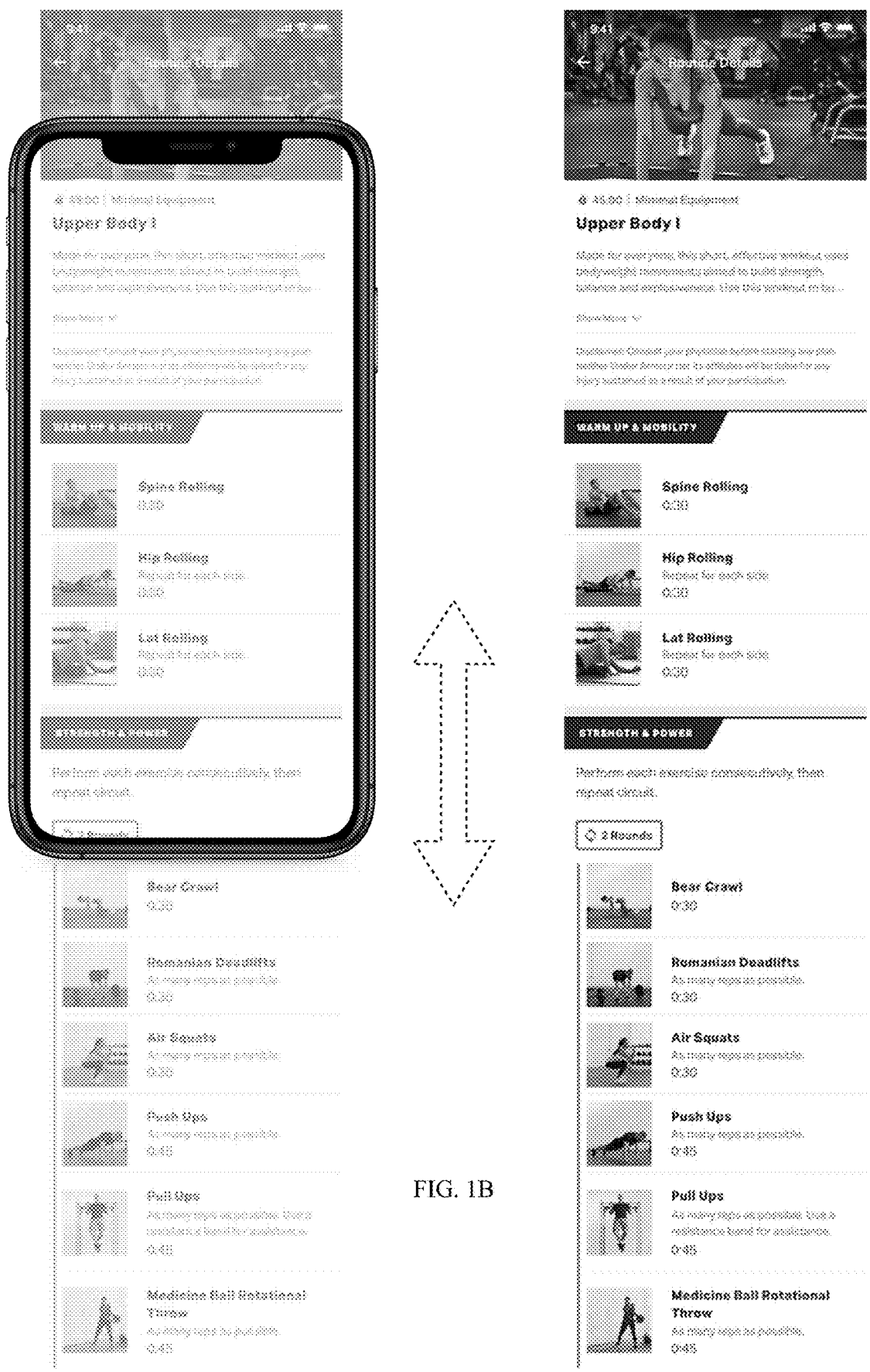
FIG. 1B is a graphical representation of a prescribed workout, useful for describing various aspects of the present disclosure.

The user is prescribed workouts based on the selected training plan. For example, the user may elect to receive their currently prescribed workout on any one of their personal devices (e.g., a smart phone, a smart watch, etc.) Prescribed workouts are delivered to the user's device and may include multiple different types of exercises. Each exercise of the workout may be associated with its own completion requirements (e.g., time, distance, repetition, etc.) FIG. 1B is a graphical representation of one such exemplary prescribed workout.

Figure 1C:
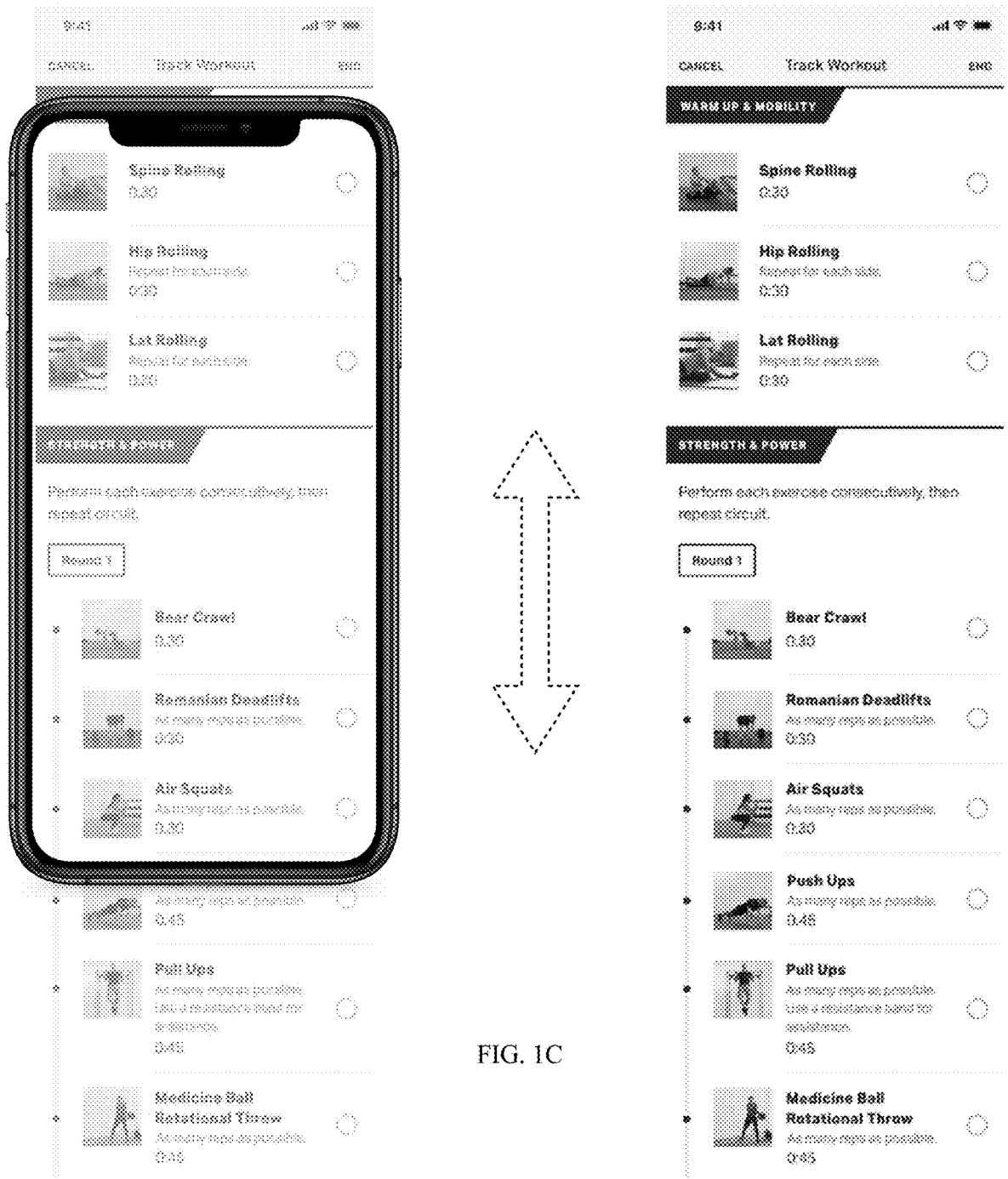
FIG. 1C is a graphical representation of an exemplary "checklist" of exercises of the prescribed workout, useful for describing various aspects of the present disclosure.

When the user starts a prescribed workout, they are guided through their workout, one prescribed exercise at a time. Specifically, a fitness tracking application running on their personal fitness device provides a checklist of exercises for the prescribed workout. FIG. 1C is a graphical representation of one such exemplary "checklist" of exercises. Notably, the workout prescribes a specific known ordering to the exercises. Each exercise can be completed by default in-sequence; where necessary, the user may skip or re-arrange exercise order. By default, when an exercise is completed, the next exercise is automatically populated based on the prescribed ordering.

The fitness tracking application generates an exercise specific user interface that may be pre-populated based on each exercise's associated prescribed completion requirement, the measurement modality, and (in some cases) the personal fitness device's user interface capabilities. In some cases, the exercise specific user interface may provide a simplified mechanism for logging the exercise progress. In one specific implementation, the user interface elements are simplified to only a few enumerated states ("start", "stop") and/or conditional (if-then) user interface elements.

As but one example, a smart phone may provide a "floating" simplified user interface component. Specifically, the simplified user interface component is accessible in the user interface foreground and overlays over other background smart phone application user interfaces. In some variants, the floating user interface component can be moved to view and/or gain access to the overlaid background user interface functionality. The floating user interface components allow a user to interact with the simplified user interface during exercise, while still allowing access to other smart phone functionality (e.g., view the prescribed workout overview, music playlist, instructional videos, etc.)

Figure 1D:
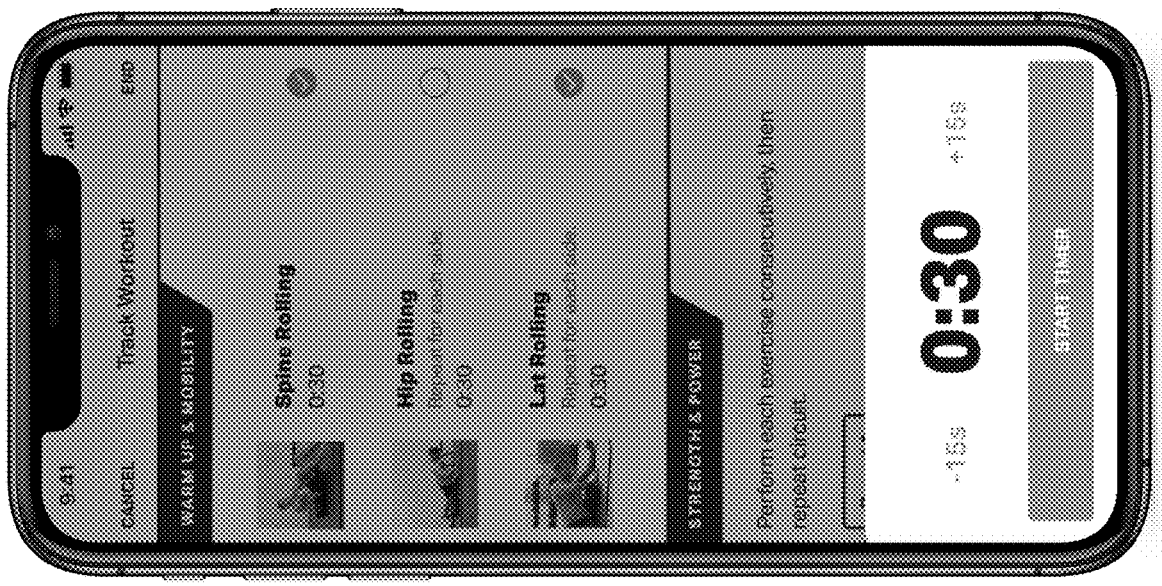
FIG. 1D is an exemplary "floating timer" user interface element, useful for describing various aspects of the present disclosure.
Figure 1D:
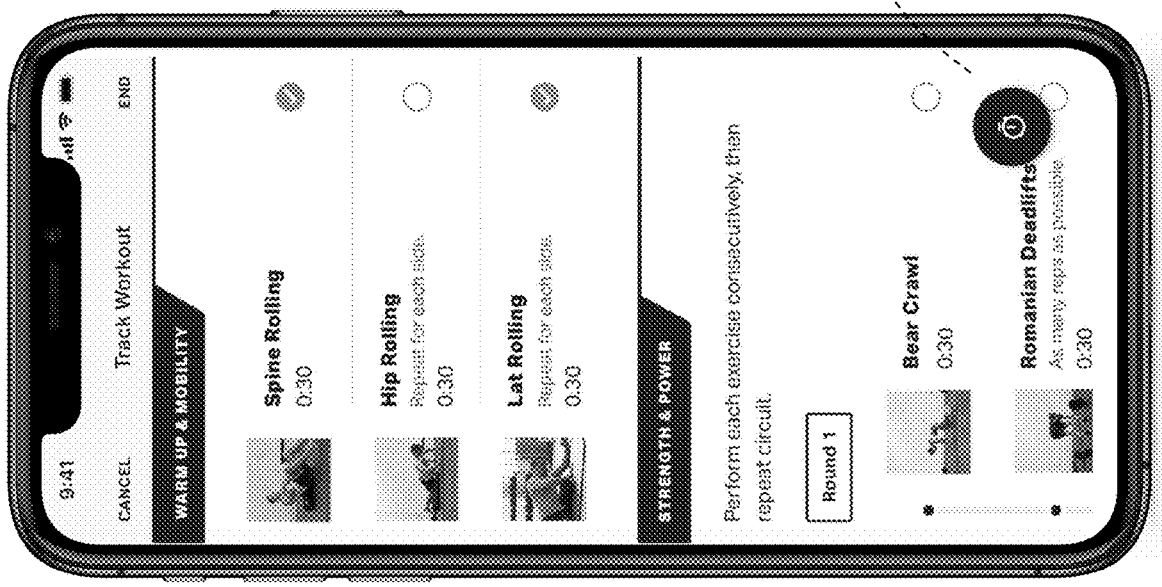

FIG. 1D provides one exemplary "smart timer" user interface element. As shown therein, the smart timer button may be used to bring up a timer interface that has been pre-populated with a prescribed value for the associated prescribed exercise (e.g., 30 s). In the illustrated embodiment, the user can modify the prescribed exercise by certain enumerated increments (e.g., add or subtract 15 s increments).

More generally, a routine timer may count down from a prescribed time or measure an elapsed time (count up to keep track of an actual time). For instance, 1 minute of jump rope may have a countdown timer. Similarly, "rounds for time" may have a stopwatch to measure elapsed time. In some cases, the smart timer interface may include visual indications as to the expected target time for completion (e.g., a target completion time of 30 seconds, etc.) In one exemplary implementation, the smart timer interface may be simplified to a "start" and a "stop" button element; in some cases, the start and stop may be the same element (press to start, press again to stop). Stopping the timer causes the fitness tracking application to record the measured time and move on to the next exercise.

Figure 1E:
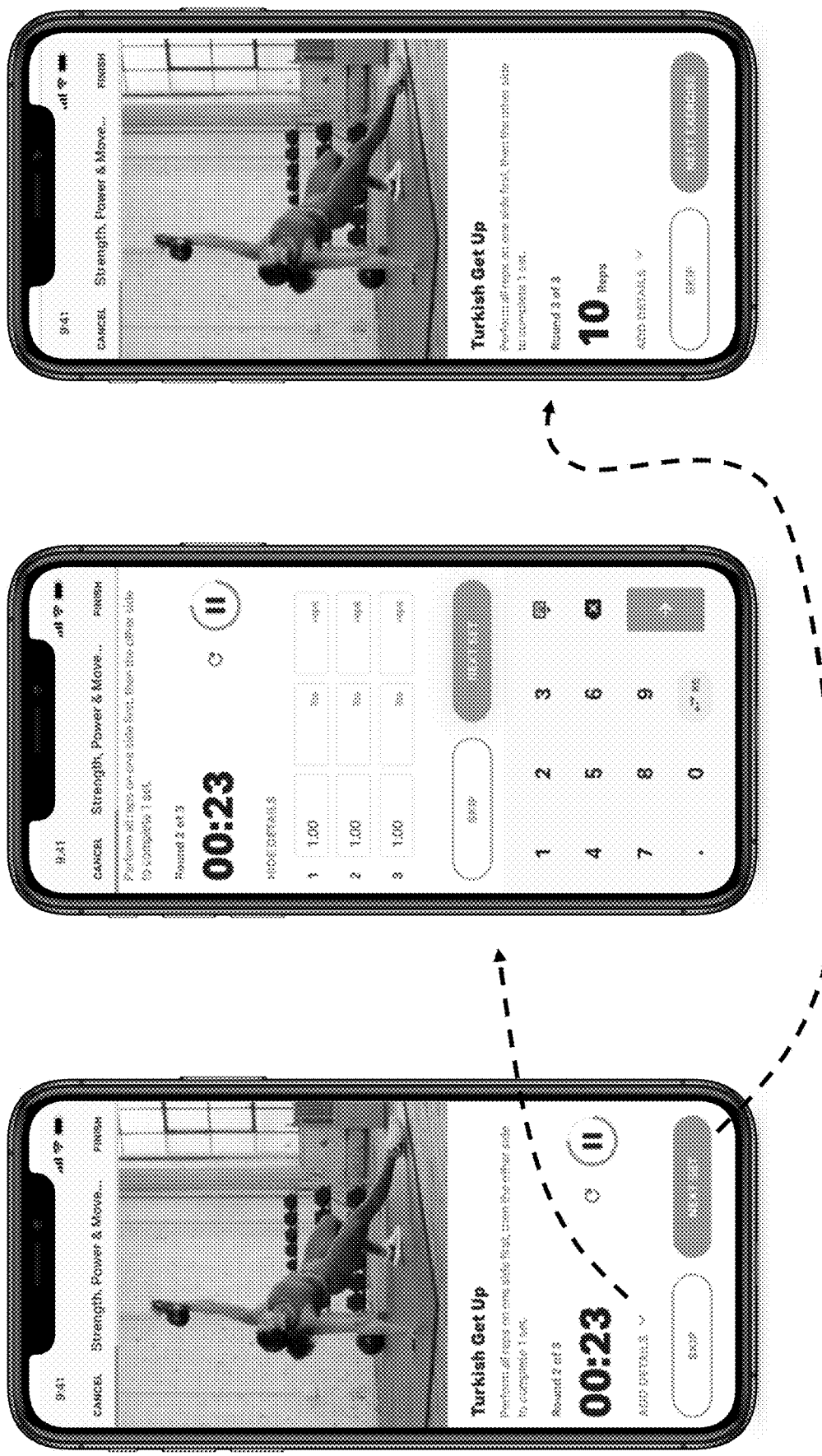
FIG. 1E is an exemplary exercise specific user interface element for manual data entry, useful for describing various aspects of the present disclosure.

FIG. 1E provides one exemplary exercise specific user interface element for manual data entry. As shown therein, the manual data entry user interface enables the user to manually modify pre-populated exercise data with additional information. For example, the user interface may be pre-populated with a prescribed duration (1:00); in some cases, the exercise specific user interface may additionally include prescribed repetition information; e.g., a suggested weight and repetition count. The user can accept the pre-scribed data and/or provide additional detail (e.g., actual weight and/or repetitions). In one exemplary implementation, the repetition counter interface may be simplified to just enumerated "skip", "next set", and "add detail" button elements. If the user selects the "next set", then the user is assumed to have completed the exercise as prescribed, and the completion values are logged. If the user "skips" the exercise, then a null set of exercise data is recorded. In some cases, the user may "add detail" where necessary (where the user decides to adjust their prescribed weight and/or repetitions.) When a user has completed all the sets in the exercise, they can proceed onto the next prescribed exercise.

While the foregoing user interface is described in the context of a time-based measurements, other measurements may be substituted with equal success. In some embodiments, a "smart repetition" counter may count down from a prescribed number of repetitions or count up to keep track of an actual number of repetitions performed. In some cases, the repetition counter may be simplified to e.g., tally mark type gestures, voice control, "next set", "skip", and/or "add detail" touch screen elements, etc. In yet another specific implementation, a "smart distance" tracker may track up to a distance (e.g., measure a distance traveled, measure a number of steps taken, etc.), or count down from a pre-scribed mileage. In some cases, the distance tracker may be simplified to e.g., start tracking, stop tracking. The distance tracker may record distance based on actual location data (e.g., GPS data), rely on manual entry, and/or record the distance as prescribed.

The user's actual exercise performance is transmitted back to the health and fitness servers. The user's workout history may be used to modify subsequently prescribed workouts and/or exercises to maximize the user's performance progression. The foregoing discussion of the exemplary implementation is purely illustrative; artisans of ordinary skill in the related arts may add, remove, and/or substitute similar functionality, given the contents of the present disclosure. More generally, various embodiments of the present disclosure ensure that users can focus their attention on their physical exertion when they are mid-workout, so as to maximize workout efficacy and improve workout intensity.

Network Architecture

Figure 2:
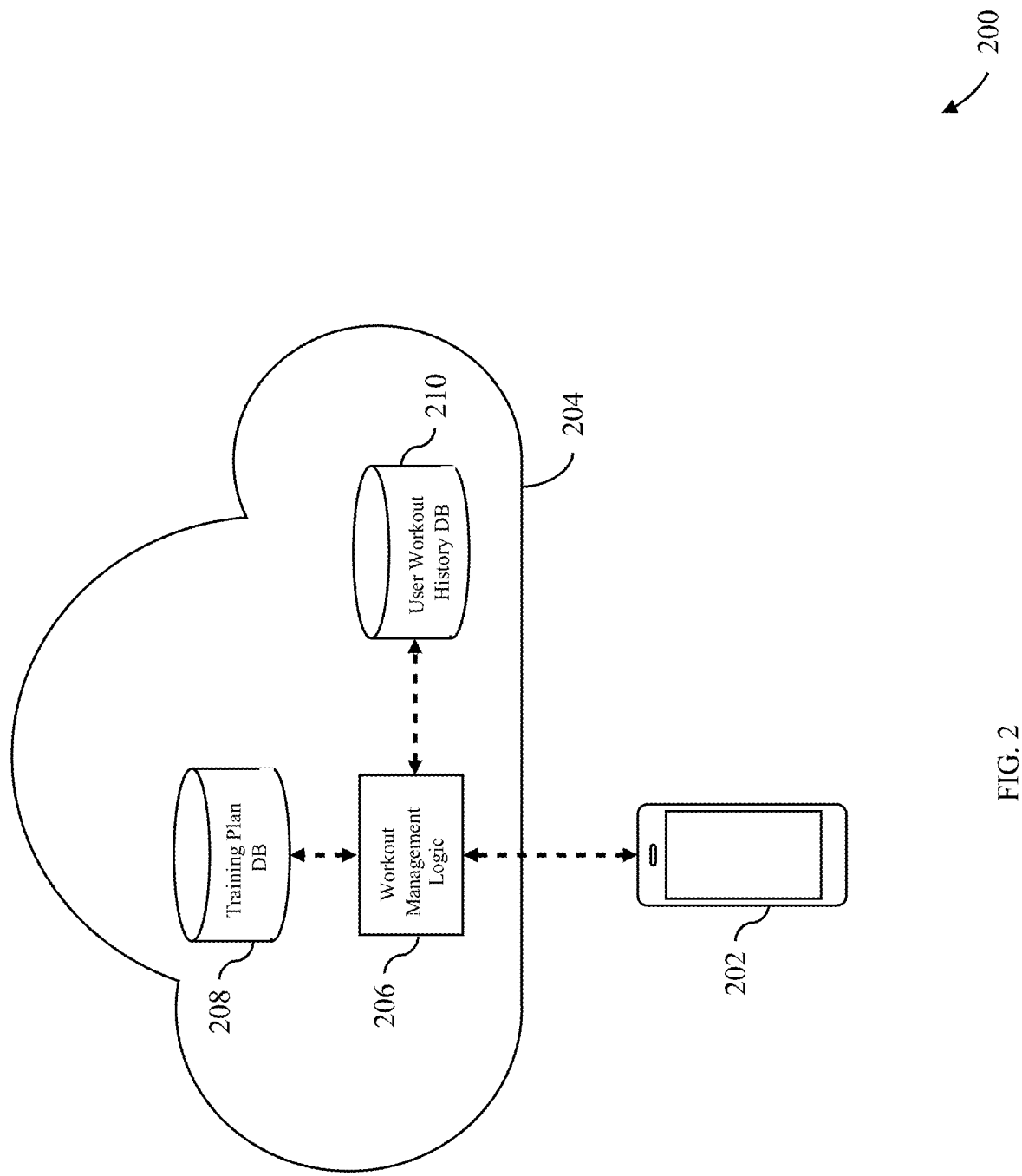
FIG. 2 is a logical block diagram of an exemplary network architecture configured to enable sequential task management via task specific user interface elements, in accordance with the various principles described herein.

Referring now to FIG. 2, an exemplary network architecture 200 configured to enable sequential task management via task specific user interface elements is shown. While the following discussion is presented in the context of a health and fitness network, the various principles of the present disclosure may be broadly applicable to any task which benefits from minimizing user distractions. More generally, the principles described herein may be applied to any prescribed action which is subdivided into sequential tasks. Other examples of activities that might benefit from task-specific user interfaces may include without limitation e.g., meal preparation, academic test preparation, habit changing applications, television timer applications, long haul driving applications, work/rest timers and/or any other such application.

As illustrated, the network architecture 200 includes one or more user devices 202 in communication with a health and fitness network 204. In one exemplary embodiment, the health and fitness network 204 may include one or more of workout management logic 206 in communication with a training plan database 208, and a user workout history database 210.

The health and fitness network 204 may include one or more wired and/or wireless, private and/or public network, including but not limited to, e.g., the Internet. The health and fitness network 204 may include, for example, a wireless local area network (WLAN), wireless wide area network (WWAN), wired network, or any other suitable communication channel. Accordingly, each of the user devices 202, workout management logic 206, and databases (e.g., training plan database 208, and user workout history database 210) are configured with appropriate networking communication interfaces. An example of wired communication interface may include, but is not limited to, Ethernet; while examples of wireless communication interfaces may include, but are not limited to, near field communication (NFC), Bluetooth, Wi-Fi, 4G or 5G LTE. It is further appreciated that various gateways, routers, switches, base stations, and so forth may be involved in facilitating and forwarding communication between the foregoing devices. Additionally, it is noted that the foregoing health and fitness network 204 may be itself, composed of several networks, such that the described components are distributed in various ones thereof. In alternative embodiments, the health and fitness network 204 may include a series of devices communicating within software via software APIs (application programming interfaces).

In one embodiment, the workout management logic 206 manages a user's personal fitness journey by e.g., identifying suitable training plans for users, prescribing workouts based on a user specific training plan, tracking the user's performance over time, and modifying the user specific training plan to maximize fitness outcomes. In one embodiment, the workout management logic 206 is embodied within a server-side application that communicates with client-side applications executed from one or more user devices 202. The workout management logic 206 can retrieve training plans from the training plan database 208 and (in some variants) provide updates thereto. Additionally, the workout management logic 206 can record user exercise activity within the user workout history database 210; the user workout history data records can be accessed by the user (e.g., for motivation, performance tracking, etc.) and/or used to modify the user specific training plans.

As used herein, the term "database" refers to a structured set of data records held within a non-transitory computer-readable medium and/or the mechanisms used to e.g., add, remove, modify, and/or query and retrieve the stored data records. The term "data record" refers to a collection of data structures that represent an association, grouping, organization, or other collection of information; common examples of data structures include without limitation: numbers (integers, floating point), values (Booleans, enumerations), characters, strings, arrays (1D, 2D, N×D, etc.), lists, hash tables, etc. For example, a database may be queried for one or more data records that satisfy a particular condition; e.g., containing a particular string, value, etc.

The training plan database 208 stores a plurality of different training plans. Each training plan may be associated with a variety of different metadata useful for classification, search, progress tracking, and/or other data management. In one embodiment, each training plan data record may be associated with a plurality of workout data records. Each workout data record may include e.g., a workout type (upper body (I, II, III), lower body (I, II, III), cardio (I, II, III), etc.), workout requirements (e.g., expected time, required equipment, etc.), and descriptive media (e.g., images, text, instructional media, etc.)

In one embodiment, each workout data record is associated with one or more constituent exercise data records. Each exercise data record may include e.g., an exercise type, prescribed values (e.g., time, distance, sets/reps, etc.), and descriptive media (e.g., images, text, etc.) As but one such illustrative example, a spine rolling exercise data record may have a prescribed value of 30 s of time and associated instruction text. In some cases, the exercise data records may be associated with instructional media (demonstrating the exercises of the workout, etc.) For example, as described in co-owned U.S. patent application Ser. No. 16/730,900 filed Dec. 30, 2019 and entitled "METHODS AND APPARATUS FOR MEDIA PLAYBACK BASED ON CUE POINTS", incorporated herein by reference in its entirety, instructional exercise videos can focus a user's attention on details of proper exercise form.

As used herein, the term "prescribe" and "prescribed" refers to one or more goals, steps, actions, procedures, tasks and/or sequences thereof, which are recommended or assigned to the user to be performed. In some cases, the prescribed value may be assigned by e.g., a health and fitness server, in other cases the prescribed value may be selected by the user. Various other techniques for specifying the expected performance of the exercises within the workout may be substituted with equal success, the foregoing being purely illustrative.

In one embodiment, the exercise data records may include prescribed values. In one specific implementation, the prescribed values may be enumerated as a closed list of values. For example, an enumerated time value may be e.g., 30 seconds, +/−15 seconds, etc. An enumerated distance may be e.g., ½ mile, 1 mile, 5K, etc. An enumerated set value may be e.g., 3 sets, 4, sets, 5 sets; similarly, enumerated rep values may be e.g., 8 reps, 10 reps, 12 reps, etc. As will be readily appreciated by artisans of ordinary skill in the related arts, given the contents of the present disclosure, enumerated time, distance, and sets/reps values can be directly used within radio box and/or checklist type user interface elements. More generally, simplified data structures can be readily incorporated within the simplified user interfaces described herein, and by extension, reduce user distraction during exercise.

In other embodiments, prescribed values may be configurable values. In some cases, the configurable values may be based on specific user preferences. For example, a user may customize their times, distances, and/or repetitions according to their own personal preferences. In other variants, data analysis can be used to personalized prescribed values based on e.g., user history. For example, a user that has never successfully completed a prescribed amount of an exercise may be throttled down to a lower value. Similarly, a user that always completes an exercise too quickly, or too easily, may be graduated to a higher prescribed value. In some cases, the workout may be changed mid-workout; e.g., a workout may include both a standard track, and alternate tracks for increased and/or decreased intensity. More generally, the various techniques described herein may be broadly combined with any personalization and/or dynamic coaching scheme; the initially prescribed exercises may be based on previous user workout history, but alternative prescribed values may be substituted mid-workout based on actual logged performance.

In some embodiments, the workout data record may include a prescribed ordering; for example, exercises may be sequentially ordered. In some embodiments, the workout data record may be loosely ordered into workout phases (e.g., a warmup and mobility phase, a strength and power phase, etc.) Loosely ordered exercises may be re-organized within the same phase; this may be useful e.g., where equipment availability may be a consideration. Similarly, the workout data record may also identify suitable alternates and/or substitutions; for example, a pull-up exercise may be substituted with bicep curls, depending on equipment availability.

In some embodiments, the training plan database 208 may be curated by healthcare professionals, coaches, celebrities, or other fitness professional. In some variants, the training plan database 208 may include user generated content; for instance, a user may be able to view, copy, modify, and/or share peer training plans. As but one example, teammates can swap workouts and/or coaches may assign workouts to their teams. Still other training plan databases may be based on crowdsourced data, analytics and/or heuristic-based curation. For example, as described in co-owned U.S. patent application Ser. No. 16/588,199 filed Sep. 30, 2019 and entitled "METHODS AND APPARATUS FOR COACHING BASED ON WORKOUT HISTORY", incorporated herein by reference in its entirety, workout completion data records for a population of different individuals may be analyzed to identify groups of similarly performing individuals. Each group of individuals may be analyzed to generate an expected profile that approximates the physiological and/or psychological traits of the group. A user's training plan can be initially selected and/or dynamically re-selected, based on their closest expected profile. More generally, artisans of ordinary skill in the related arts will readily appreciate that any type of training plan may be substituted with equal success, the foregoing being purely illustrative.

The user workout history database 210 stores a plurality of user data records and their corresponding workout and/or exercise completion data records. Each user data record may include detailed information with regard to e.g., accuracy of data, fitness goal definition, progression of performance, psychological parameters (e.g., behaviors, motivations, etc.), height, weight, age, sex, ethnicity, and/or any number of other user specific parameters. Each completion data record may include detailed information with regard to e.g., date/time of past workouts, type and/or completion status of associated exercises, exerted muscle groups, duration of exertion, intensity of exertion, absolute load, relative load, range of movement, repetition, recovery time, fatigue, dynamic feedback/user response, frequency of revision, revision success/failure, and/or any number of other completion specific parameters. More generally, artisans of ordinary skill in the related arts given the contents of the present disclosure, will readily appreciate that virtually any data regarding either the individual users and/or their specific workout history can be stored.

During operation, the workout management logic 206 provides training plans to client-side applications executing on user devices 202. As but one such example, a user selects a training plan during an onboarding process and receives associated workouts for scheduling within the user's fitness tracking application. In some cases, the training plan and workout progress may additionally be scheduled and tracked at the health and fitness network 204 by the workout management logic 206 in conjunction with the user workout history database 208; in some cases, the workout management logic 206 may actively push workouts to client-side devices. For example, as described in co-owned U.S. patent application Ser. No. 16/696,232 filed Nov. 26, 2019 and entitled "METHODS AND APPARATUS FOR TRAINING PLAN DELIVERY AND LOGGING", incorporated herein by reference in its entirety, a fitness tracking system: generates a training plan based on user workout history and/or user input. Thereafter, suggested workouts can be pushed to the user's community of personal devices, via a coordinating device (e.g., a smart phone). More generally, artisans of ordinary skill in the related arts will readily appreciate that any type of workout delivery may be substituted with equal success, the foregoing being purely illustrative.

It is appreciated that in the illustrated embodiment, the aforementioned databases (208, 210) are separate and distinct from the workout management logic 206 and/or user device(s) 202. However, in other variants, the databases may be incorporated in part or in whole with either the workout management logic 206 and/or the user device(s) 202 for storage thereat. For example, workout data records may be cached locally at a particular user device 202 until e.g., the user has time to perform the workout. Additionally, or in the alternative, completion data records (in whole or in part) may be stored at the user workout history database 208 and portions may be made accessible to particular devices 202 when queried and/or locally cached. Any combination of the foregoing configurations may be utilized with equal success.

Methods

Figures 3A, 3B:
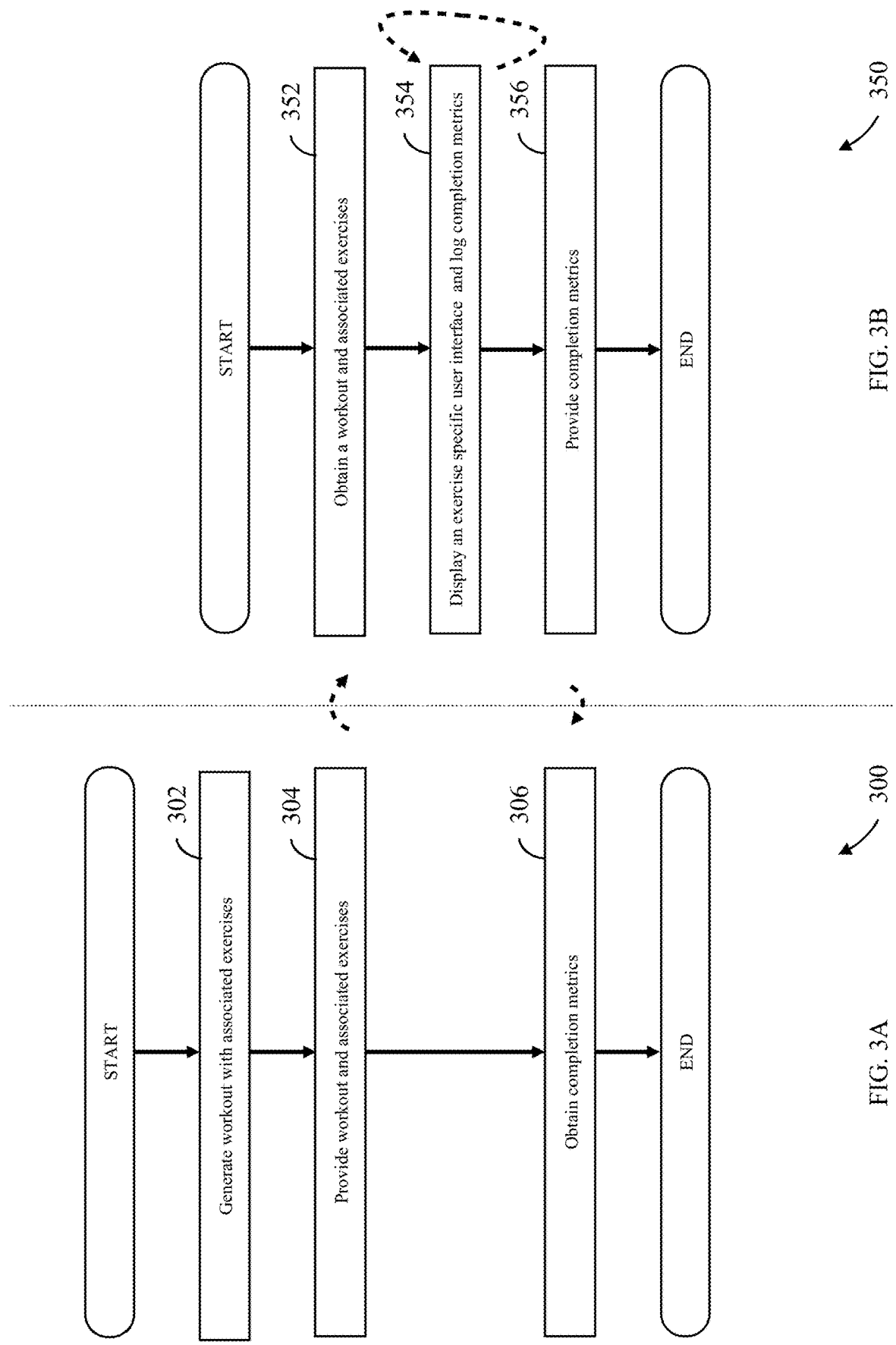
FIGS. 3A-3B are logical flow diagrams of exemplary methods for (i) managing sequential tasks via task specific user interface elements, and for (ii) controlling a sequence of tasks and logging task completion metrics via task specific user interfaces, in accordance with the various principles described herein.

FIG. 3A is a logical flow diagram of an exemplary method 300 for managing sequential tasks via task specific user interface elements, in accordance with the various principles described herein.

At step 302 of the method 300, a workout and one or more associated exercises is generated. In one embodiment, the workout may be part of a broader training plan. As but one such example, a user may complete an onboarding program with a health and fitness service. The health and fitness service can recommend different training plans to the user based on e.g., onboarding information. In some cases, several training plans can be suggested to the user along with one or more "best fit" recommendations. The user can select one of the training plans and/or may even further customize a training plan based on their particular needs. Common examples of onboarding information may include e.g., fitness goals, scheduling information and/or other user specific information.

In one embodiment, a workout is composed of one or more exercises. In some embodiments, exercises may be sequentially ordered, loosely ordered, or unordered. As used herein, the term "loosely ordered" refers to a subset of exercises in a workout which may be performed in an arbitrary sequence. Loosely ordered exercises may be grouped into phases; e.g., a first phase, a second phase, etc. In some embodiments, workouts may identify a set of alternate exercises that may be interchangeably substituted. For example, a workout may identify a set of different chest exercises (pushups, bench press, barbell press), the user may select or be assigned one of the chest exercises based on dynamic workout considerations. Relevant considerations may incorporate user selection/preference, location, time, and/or equipment availability information to select the appropriate exercise for the user.

More generally, workouts may incorporate a variety of different exercise substitution heuristics. As one illustrative example, workouts may dynamically substitute exercises based on the user's rate of perceived exertion (RPE). A user that is having difficulty with chest exercises may be switched to a lower intensity chest exercise, or possibly a completely different muscle group exercise altogether. As but another example, a user at home may not have the equipment to do a bench press or barbell press, thus the user device can automatically select pushups. In contrast, when the user is at the gym, the user device can select bench press or barbell press based on likely availability (e.g., the bench press may have limited availability during peak gym hours, barbells may be available throughout the day, etc.)

In some cases, exercises may include many different states and/or accompanying transition conditions; for example, each set of repetitions may be a discrete state, similarly mile splits of a multi-mile run may be treated as discrete states. In some variants, workouts may include rest periods; the rest period timer measures the amount of time that a user should consider resting. In a similar example, an exercise can define a "pause state" that pauses metric collection mid-activity; this may be useful for e.g., water breaks, etc. More generally, virtually any multiplicity of different states and/or transitions may be identified and/or enumerated.

In one embodiment, the workout and one or more associated exercises is generated by a health and fitness network based on the user's previous workout history. For example, the health and fitness network may identify the next workout based on the user's progress within a pre-defined training plan. In other embodiments, the workout may be generated on an as-needed basis; for example, the health and fitness network may analyze the user's current performance progression and generate a workout therefrom. As but another example, a health and fitness server may start with a basic workout template, and custom tailor individual exercises based on e.g., the user's location, the time of the workout, the availability of equipment, etc.

More generally, artisans of ordinary skill in the related arts, given the contents of the present disclosure, will readily appreciate that the various principles described herein may use a broad range of techniques to generate the workouts described herein. Workouts may be created, obtained, modified, and/or updated based on data analysis, user history, and/or other heuristics. In some embodiments, $2^{nd}$ and/or $3^{rd}$ party sources may provide information to assist in the creation, procurement, modification, and/or updating of workouts. Examples of such $2^{nd}$ and/or $3^{rd}$ party sources may include e.g., other fitness services, social networks, peer devices, medical and/or other personal services, etc. In some cases, workout creation, generation, and/or modification may be assisted in whole or part, by human input; examples of human input may include e.g., health expert analysis, fitness professional analysis, celebrity athlete generation, crowdsourced generation, etc.

At step 304 of the method 300, the workout and its one or more associated exercises are provided for workout tracking. In one embodiment, the workout and its one or more associated exercises are provided to a user's personal device. As used herein, the term "personal device" refers to a set of devices associated with a user. The association may be permanent, temporary, or some variant thereof. As but one such example, a smart phone may identify nearby smart exercise equipment and push workouts thereto and/or receive workout data therefrom. Consider a communal smart stationary bicycle provided as part of a weekly cycling class membership at a user's gym. The user's smart phone may notify the user when it is time to go to cycling class. The smart bicycle may associate (pair) with the smart phone (e.g., a "reserved seat in class") and also collect the user's workout metrics during cycling class (e.g., distance, time, cadence, calories burned, etc.) Similar techniques may be used for treadmills, rowing machines, weightlifting machines, and/or any other so-enabled exercise equipment.

In one embodiment, the workout and its one or more associated exercises are transmitted to a user device as part of a training plan. Providing the training plan in its entirety may enable relatively infrequent networking transactions between the user device and the health and fitness network. More directly, reducing network transactions to one bulk training plan transfer and small infrequent updates may greatly reduce overall synchronization and/or connectivity requirements. Alternatively, the workouts may be transmitted to the user device one (or a few) at a time. Providing workouts on a frequent basis may provide the health and fitness server more opportunities to e.g., modify workouts based on performance progression. Still other variants may utilize a hybrid of the foregoing; for example, a user that consistently performs in accordance with their training plan may only infrequently require a bulk transfer of new workouts. In contrast, a user that inconsistently exercises may require frequent revisions and/or updates.

More generally, artisans of ordinary skill in the related arts, given the contents of the present disclosure will readily appreciate that the transaction may be made more or less granular depending on application considerations. For example, the workouts may be provided in subdivided portions (down to the exercise, if necessary). Similarly, a library of many possible workouts may be provided in a single lump download.

In some embodiments, the workout and one or more associated exercises may be signed to provide certification of authenticity. A digital signature provides a secure method to certify the source of a data structure, and that the data structure has not been tampered with in transit. As previously alluded to, the various methods and apparatus described herein may be leveraged by an entire community of different services to provide a richer and more varied ecosystem of fitness applications. However, personal information is sensitive, and should be protected from malicious parties. Thus, access to certain personal information and/or the provisioning of training plans, workouts, and/or exercises may be limited. For example, a $1^{st}$ party health and fitness server (e.g., such as is administered by the Assignee hereof) may have the highest access rights and/or unfettered provisioning capabilities. In contrast $2^{nd}$ party affiliates (trusted) and/or $3^{rd}$ party (untrusted) applications may be designed to interface at lower privileges and/or access rights. In some cases, certifications may be dynamically updated (such that new parties may be added, and stale or compromised parties removed).

While the foregoing discussion is presented in the context of a health and fitness server that provides workouts to a user device via a network connection (e.g., wireless network, cellular network, wired network, etc.), virtually any other technique for workout generation may be substituted with equal success. For example, a user may download workouts from the internet, locally generate the workouts at their personal device, exchange workouts with peer devices, and/or any other ad hoc workout procurement technique common within the consumer electronic arts.

At step 306 of the method 300, completion metrics for one or more associated exercises are obtained. In one embodiment, completion metrics may be bundled and received throughout the workout, post-workout, or even post-training plan. In some cases, a workout or training plan may be completed in its entirety (in addition to, or in lieu of individual exercise completions). Notably, completion metrics are provided back to the health and fitness network for user history and/or possibly to modify subsequent training plan/workout provisioning, the granularity of reporting may be adjusted based on the level of detail that is most useful. In other words, workout/training plan completions may be sufficient if individual exercise progress is not actively being tracked, modified, etc.

In one embodiment, completion metrics may be received on a periodic basis (e.g., once a day, once a week, once a month). In other embodiments, completion metrics may be received at specified events (e.g., completion of a workout, completion of a set of workouts, etc.) As but one such example, a user may complete an initial set of workouts (e.g., Cardio I, Upper Body I, Lower Body I); the completion metrics may be used to determine whether the user should stay at the current training plan, progress to a harder training plan, or scale down to an easier plan. Still other implementations may receive completion metrics based on user device and/or network availability considerations. For instance, an outdoors trail runner may often be outside of network coverage, their user device may store up completion metrics for a set of trail runs and perform reporting once the user device re-enters network coverage. In other variants, a user device may record until its memory exceeds a threshold amount of data; the threshold amount of data may be increased or decreased so as to result in more or less frequent reporting.

In some embodiments, exercises may be completed with default completion information; for example, a user that is assigned a 5-mile run may not care how far they actually run. Similarly, in some embodiments, exercises may have null set completion data. Default and null set completion data may be used where e.g., no actual metrics are available, where the user back annotates their fitness log, or simply where the user does not care to track their actual metrics.

In other variants, the completion metrics may be reported according to the prescribed completion criteria. In some variants, completion criteria may be a "closed" value that specifies a minimum/maximum number of repetitions, duration, distance, and/or other determinate value. In other embodiments, the exercises may be associated with an open-ended value. An open-ended value may be a running count of actual repetitions, a measured duration, a measured distance, and/or other measured value.

In some embodiments, the completion metrics may include a hybrid of the foregoing completion types. For example, a user may complete a subset of exercises as prescribed but fail to complete the remaining exercises; the completed exercises may be reported according to default closed value completion metrics, the incomplete exercises may be reported with an open-ended degree of completion. In some cases, additional performance data may be included; examples of useful data may include without limitation, user input (e.g., rate of perceived effort (RPE)), biometric data (e.g., heart rate, blood oxygen, etc.)

While the foregoing discussion is directed to completion metrics provided by a user device, artisans of ordinary skill in the related arts will readily appreciate that the principles described herein may be readily applied to time shifted data analytics. In some such cases, the user may not directly interface with the device at the time of the exercise. Instead, the data collected by the device can be used to "reconstruct" the user's actual workout metrics using data mining techniques. As but one such example, a user may be prescribed a set of timed exercises; the heart rate monitor can be used to extract, and log actual completion times based on spikes in heart rate over time. As another example, a user may be prescribed a set of distances and use a pedometer (or smart shoe) to capture step count and step rate metrics. Subsequently thereafter, the pedometer metrics can be used to extract, and log actual distances completed. In some cases, a user may manually verify and/or post-annotate workouts; checking data analytics can greatly improve the convenience of post-workout logging and accuracy of such logs. While the foregoing examples are described in the context of pedometers and/or heart rates, artisans of ordinary skill in the related arts will appreciate that any apparatus for collecting physiological data may be substituted with equal success; common examples include, without limitation: accelerometers, pedometers, magnetometers, blood sensors, microphones, cameras, etc.

FIG. 3B is a logical flow diagram of an exemplary method 350 for controlling a sequence of tasks and logging task completion metrics via task specific user interfaces, in accordance with the various principles described herein.

At step 352 of the method 350, the workout and its one or more associated exercises are obtained. In one embodiment, the workout and associated exercises are received from a health and fitness server. In other embodiments, the workout may be obtained as a standalone workout and/or created based on a set of exercises. As but one example, a user may be able to create a custom workout to suit their personal needs. In a related embodiment, the user may be part of a community of users that share workouts. For example, some fitness organizations generate workouts for their members as part of the membership (e.g., a new workout every day, week, month, etc.) In another such example, a gym may publish workouts as part of a gym goer fitness education initiative, to popularize new equipment, and/or to load balance users throughout during peak hours. In yet another example, a coach may assign, or an athlete may run through, a standardized workout to e.g., make apples-to-apples comparisons with other athletes. In still other examples, a celebrity athlete may be able to curate their own library of workouts and/or potentially monetize access to their library. As previously alluded to, a user's personal information is sensitive, and should be protected from malicious parties. Thus, peer-to-peer based workout sharing applications may implement authentication and/or privacy settings.

In one exemplary embodiment, different exercises of the workout may have different user interface requirements. For example, certain exercises may use a timer, counter, or distance tracker. Exercise specific user interface capabilities may be determined based on the workout and/or exercise modality. As but one such example, the timed exercise may use a start/stop timer that is represented with a "start" and a "stop" button element; in some cases, the start and stop may be the same element (press to start, press again to stop). In some variants, the smart timer may be "floating" over (and moved to uncover) background applications. In some cases, the timer may count down from a prescribed value, or count up to measure an elapsed time. In some cases, the smart timer may provide related information such as e.g., split times, historic times, personal best times, etc.

In another embodiment, an exercise for distance may use a start/stop distance tracker that may be represented with a "start" and a "stop" button that starts and stops location tracking (or step counting, or similar distance metric). In some cases, the distance tracker may provide related information such as e.g., average pace, heart rate, cadence, current location on a map, etc.

In yet another embodiment, a repetition counter may count down from a prescribed repetition or count up. In some cases, the prescribed repetition count may be automatically recorded as the completed count if the user selects a "next exercise" button. If the user selects the "add detail" button, then the user can provide an open-ended completed repetition value. In some cases, the repetition counter may provide related information such as e.g., current set, next set, previous set, historic performance, personal best, etc.

In one embodiment, the user device generates the exercise specific user interface based on its user interface capabilities. In other words, different user devices may have different user interface options and capabilities; consequently, different devices may treat the same workout differently. As but one such example, a smart phone device may provide e.g., touchscreen, microphone, speaker, GPS, and/or other capabilities. In contrast, a smart watch may have limited interface capabilities (reduced touchscreen, little to no audio), but provide e.g., heart rate tracking, and haptic sensors. Notably, a workout that is provided to the smartphone may be use smartphone capabilities (e.g., distance running may use GPS, floating routine timers displayed via the touchscreen, etc.) In contrast, workouts that are provided to the smart watch may be modified (e.g., running based on heart rate and step counts, haptic/vibrator-based user interfaces, etc.)

As a brief aside, one burgeoning field in consumer electronics is the so-called "wearables" market. Wearable devices are intended to be worn during everyday activity; usually, wearable devices trade-off functionality, user accessibility, and/or processing power for other considerations e.g., style, aggressive form factors, reduced power consumption, and durability (weather resistance, etc.) For example, a smart watch or smart shoes may focus on style and fit rather than e.g., a large screen or high-performance processing. Moreover, wearable form factors minimally interfere with movement and/or mobility e.g., wearables are not "held" with hands nor do they distract from the user's attention. In particular, most wearables are designed to unobtrusively use e.g., tactile, haptic, auditory, and/or time-insensitive visual interfaces.

More generally, the principle of simplifying user interface elements consistent with exercise specific considerations (such as the data to be captured during an exercise, the user device available to measure performance, etc.) may be broadly extended to encompass a variety of different considerations. In some embodiments, a user may be able to reduce the functionality of the exercise specific user interface based on well-known workouts. For example, a trail runner may be provided with a listing of their most frequently run trails; the trail runner can select the specific trail they want to run currently. The workout can be logged using the trail runner's historic logged mileage for the selected trail, subsequent user interface interactions can be greatly reduced (if not altogether eliminated) and the user can run with minimal distraction.

In some embodiments, workouts may be specifically assigned or selected based on the exercise specific user interface capabilities and/or support. As a brief aside, sifting through a myriad of workouts can be a tedious process. Many different techniques may be used to enable users to conveniently identify workouts that are suitable for their needs. Notably, the exemplary exercise specific user interface applications described within the present disclosure provide for reduced distractions during workouts, which can result in a better user experience. Thus, in some cases, users may filter their workout programs based on exercise specific user interface capabilities. For example, a user that is looking for suitable training plans may limit their searches to e.g., workouts that use exercise specific user interfaces on a smart phone. In some cases, the user may further limit their searches based on the type of user interface e.g., floating user interfaces, haptic or voice-controlled interfaces, "checklist" type interfaces, etc.

In one embodiment, the user device may prepare the workout based on local information (user preferences, time, equipment, etc.) As previously noted, the workout may be composed of one or more exercises which may be ordered, loosely ordered, or unordered. In one embodiment of the present disclosure, the proposed workout may be displayed to the user, so that the user can make any initial modifications prior to the workout. For example, the user may receive a workout that includes e.g., sit-ups, push-ups, pull-ups, and a run; the user may elect to add, remove, or modify an exercise prior to the workout. Taking care of such modifications ahead of time can greatly reduce user distraction mid-workout.

In a related embodiment, the user device may automatically add, remove, or modify the exercises of the workout based on its local information (e.g., sensed conditions, user configuration, runtime information, etc.) For example, the user device may modify the workout based on location, time, and/or weather conditions. Similarly, the user device may automatically modify workouts based on user preferences and/or user schedule information; e.g., a user may prefer certain exercises over others, upcoming scheduled appointments may put hard time limits, etc. Similarly, the user device may select workouts depending on how the user intends to monitor their exercise. For instance, the user device can determine if it senses movement (is being held), ambient noise, orientation, etc. As but one such example, a user that has set their smart phone down and is using voice instructions may be offered a different set of workouts and exercises than a user that is wearing their smart phone in an arm wrap.

At step 354 of the method 350, the user device displays exercise specific user interfaces and logs completion metrics for each exercise. Various aspects of the present disclosure leverage the prescribed nature of a workout (e.g., the known range of data to be captured and/or the known sequence of exercises) to monitor and/or coach the user through their workout with minimal distraction. The planned nature of workouts can greatly simplify the requirements for user interaction. Specifically, in one embodiment, the user device displays an exercise specific user interface. The exercise specific user interface is configured to enable the logging of expected completion data (if any) for an exercise and/or the known sequence of the exercises. Additionally, the exercise specific user interface provides one or more user interface elements that e.g., log a prescribed completion metric and/or causes transition to another exercise of the workout in a prescribed sequence.

In one embodiment, each exercise of the workout has a start condition and a stop condition. The start condition identifies how the user device transitions into the exercise activity (e.g., pressing a start button, increasing above a threshold heart rate, etc.) In some cases, the start condition may additionally identify the modality of exercise measurement (e.g., counting repetitions, duration, distance, etc.) The stop condition identifies how the user device transitions out of the exercise activity (e.g., pressing a stop button, falling below a threshold heart rate, etc.) In some cases, the stop condition may additionally define how to format the measured exercise data into completion metrics (described in greater detail infra). In some embodiments, the stop condition may also identify the start transition for the next exercise activity. In other embodiments, the stop condition may trigger an evaluation step to identify the next exercise (e.g., where the user device may need to identify which exercise to assign to the user next).

In one embodiment, the exercise data is a prescribed exercise duration and the user interface element may be a "start" and "stop" button element; in some variants, the "start" and "stop" may be the same element (press to start, press again to stop). The "start" button starts a timer mechanism, and the "stop" button stops the timer mechanism and automatically logs the elapsed time. In one such embodiment, the elapsed time corresponds to the expected completion time for the exercise. In some cases, the "stop" button directs the user to a checklist of remaining exercises to select the next exercise; in other cases, the "stop" button may transition to the next exercise. In one such implementation, the next exercise corresponds to the next exercise in the known sequence of exercises.

In one embodiment, the exercise data is a prescribed number of exercise repetitions and the user interface element may be a "add detail" and "next" button element. The "next" button logs the predetermined number of exercise repetitions and directly links to the next exercise (or returns to the checklist of remaining exercises). The "add detail" button allows the user to manually log exercise information (e.g., a weight, a repetition number, etc.)

In one embodiment, the exercise data is a prescribed distance of travel and the user interface element may be a "start" and "stop" button element; in some variants, the "start" and "stop" may be the same element (press to start, press again to stop). The "start" button starts a distance tracking mechanism (e.g., pedometer, GPS, etc.), and the "stop" button stops the distance tracking mechanism and automatically logs the tracked distance. In one such embodiment, the tracked distance corresponds to the expected completion distance for the exercise. In some cases, the "stop" button directly links to the next exercise (or returns to the checklist of remaining exercises).

While the foregoing examples are presented in the context of specific modalities of exercise measurement (e.g., counting repetitions, duration, distance, etc.) registered via a touchscreen interface, other modalities and/or user input may be substituted with equal success. For example, the user interface element may be haptic input for a haptic interface (e.g., a tap-based input with vibrator acknowledgement). In still other variants, the user interface element may be audible commands and audible acknowledgement for a voice-controlled interface. In yet another variant, the user interface element may incorporate a vision recognition system (for responding to visual signals, such as physical gestures.) As but one such example, a user wearing a heart rate monitor may be told to keep their heart rate above a threshold for a certain amount of time. Examples of other modalities include without limitation: cardiovascular strain, caloric consumption, muscular exertion, fatigue, blood oxygenation, lactate production, blood occlusion, nervous system activation, temperature increase, sweat production, changes to form/body positioning (via video analysis), audible data (exhalations, foot strikes, etc.), and/or any other physical effect of exertion.

In one exemplary embodiment, the exercise specific user interface is a floating widget that overlays background applications. In other variants, the exercise specific user interface is a foreground application. In yet other variants, the exercise specific user interface may be displayed in parallel with other applications in the foreground. As a brief aside, a "foreground" application refers to an application that is configured for "active use" by the user; foreground applications are treated with a higher priority for processing and memory resources than background applications. "Background" applications refer to applications that are allocated processing and memory resources when available (only when necessary). Within the context of user interface applications, floating user interface components are treated at a higher priority than the background that is overlaid (in some cases, the backgrounded applications can be suspended).

While the foregoing discussion is presented in the context of user interface elements that greatly simplify the user interface, the various principles described herein may be extended to enable e.g., logging of multiple predetermined completion metrics, or transitioning to any number of other exercises of the workout. As but one such example, some exercises may include many different states and/or accompanying transition conditions; for example, each set of repetitions may be a discrete state, similarly mile splits of a multi-mile run may be treated as discrete states. In a similar example, an exercise can define "rest breaks" between different exercises, and "pauses" that pause metric collection mid-activity (this may be useful for e.g., water breaks, etc). More generally, virtually any multiplicity of different states and/or transitions may be identified and/or enumerated.

In the foregoing illustrative discussions, the exercise specific user interface is visualized according to prescribed exercise considerations. In some variants, users may further configure their visualizations; in some cases, visualizations can be less distracting and/or a source of motivation. As but one such example, a timer interface may be configured as e.g., a digital readout, a running hourglass, an analog watch face, etc. Similarly, a repetition counter may provide a running total of repetitions, a remaining number of repetitions, a set count, etc. A step counter or other distance tracking visualization may provide e.g., a percentage complete, a "field track" visualization, etc.

At step 356 of the method 350, completion metrics for one or more associated exercises are stored and/or transmitted. In one embodiment, the completion metrics may be batched (by workout, training plan, or other schema) and transmitted based on e.g., memory, battery, network availability, and/or any number of other considerations.

In one embodiment, the completion metrics may be monitored for opportunities to modify the workout. As previously alluded to, the user device may continuously monitor the user's exercise performance. Consequently, various embodiments of the present disclosure may additionally simplify workout adjustment on-the-fly. Specifically, while the foregoing examples are provided in the context of a known sequence of exercises, more complex variants may allow for additional known alternate sequences of exercises. For instance, a user may start a workout, but quickly realize that their workout is too difficult or easy; instead of stopping their workout and trying to identify a better fit, the user interface may offer an on-the-fly quick switch button that changes the workout to an alternate track. In a related embodiment, the completion metrics may also be used by the user device to automatically modify the next exercise (without distracting the user). In some situations, the user may be notified that the workout has been adjusted based on their performance such that the user may override the adjustment if desired.

While the foregoing example is presented in the context of a workout of exercises, artisans of ordinary skill in the related arts will readily appreciate that the various principles described herein may be readily adapted to other applications. In one such example, as described in co-owned U.S. patent application Ser. No. 16/580,435 filed Sep. 24, 2019 and entitled "METHODS AND APPARATUS FOR RECIPE DISCOVERY AND CONSUMPTION LOGGING", incorporated herein by reference in its entirety, recipes may be curated and tagged from a variety of sources such as health and fitness blogs and/or other articles of interest. In one such case, a user can browse through and identify recipes to prepare; once selected, the user can be guided through recipe preparation. Certain recipe steps may provide a smart timer that is pre-populated with the prescribed cooking times. In some variants, the recipes may also support ad hoc user modifications to recipe instructions. Different users may use different cooking times for the same recipe; as but one such example, some users may prefer more chewy cookies, whereas others prefer crisp wafer like cookies. In such cases, the user recipe modifications can be stored off for future reference.

In another such example, a test preparation application may break up a test preparation training plan into a series of problem sets (e.g., mathematics, verbal, reading comprehension); each problem set can be associated with required completion metrics (e.g., percentage correct, total duration, total questions answered, etc.) During test preparation runs, the user's test preparation application provides a smart timer that is pre-populated with the appropriate work times, etc.

Apparatus

Figures 4A, 4B:
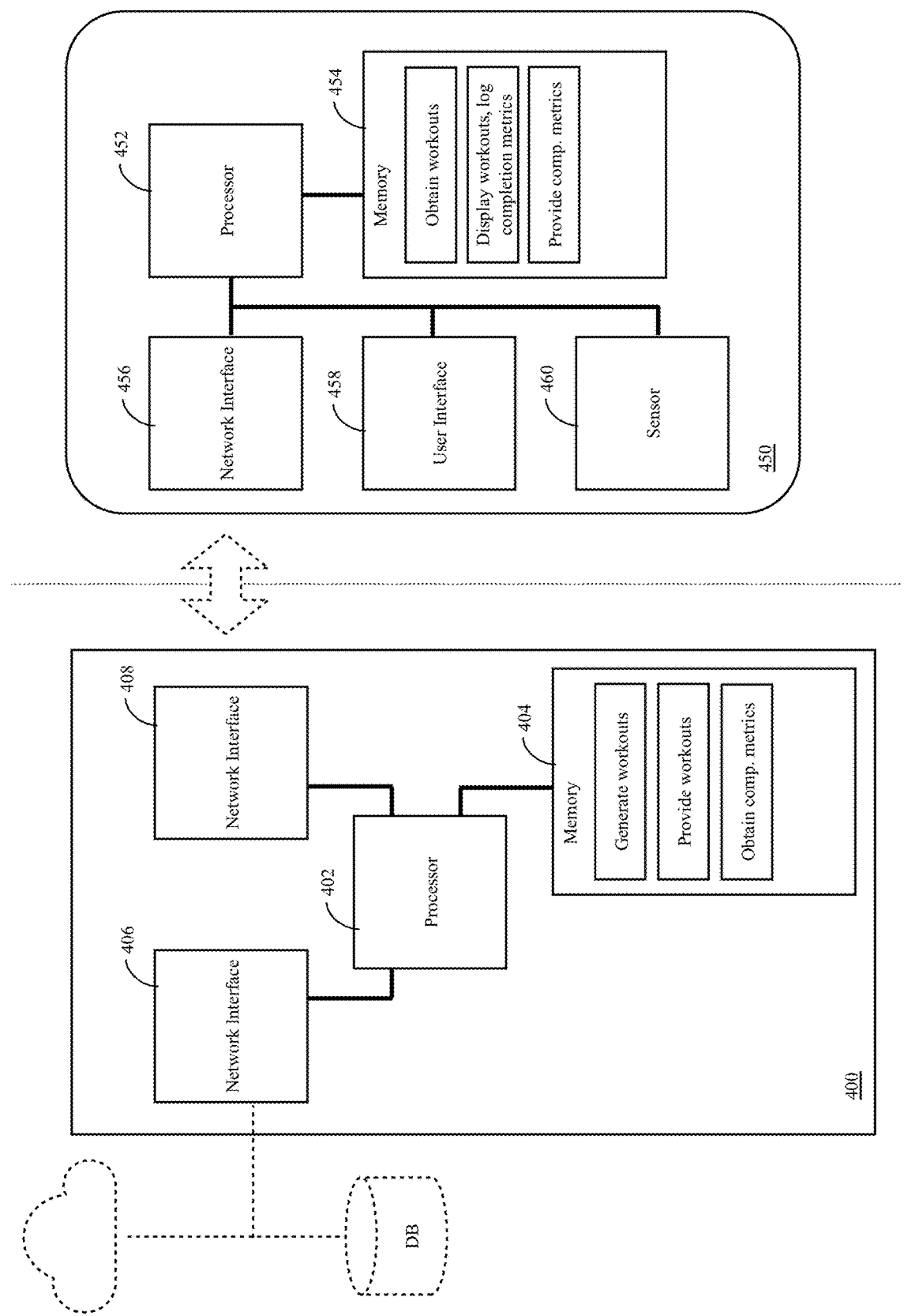
FIGS. 4A-4B are logical block diagrams of exemplary server apparatus, and client device, in accordance with the various principles described herein.

FIG. 4A is a logical block diagram of one exemplary server apparatus 400, useful in accordance with the various principles described herein. In one embodiment, the server apparatus 400 includes a processor 402, non-transitory computer-readable medium 404, and one or more network interfaces (e.g., a first network interface 406, and a second network interface 408).

The components of the exemplary server apparatus 400 are typically provided in a housing, cabinet or the like that is configured in a common manner for a server or related computing device. It is appreciated that the embodiment of the server 400 shown in FIG. 4A is only one exemplary embodiment of a server 400 for the health and fitness system. As such, the exemplary embodiment of the server 400 described herein with reference to FIG. 4A is merely representative of any of various manners or configurations of servers or other data processing systems that are operative in the manner set forth herein.

The processing circuitry/logic 402 of the server 400 is operative, configured, and/or adapted to operate the server 400 including the features, functionality, characteristics and/or or the like as described herein. To this end, the processing circuit 402 is operably connected to all of the elements of the server 400 described below.

The processing circuitry/logic 402 of the host server is typically controlled by the program instructions contained within the memory 404. The program instructions 404 are configured to manage workouts via exercise specific user interfaces, as described in further detail supra. The health and fitness program at the server 400 may be configured to communicate with and exchange data with a client-side application running on a processor of a personal device. In addition to storing the instructions, the memory 404 may also store data for use by the health and fitness program. As previously described, the data may include the workout data records, exercise data records, and completion data records.

The network interfaces of the server 400 allow for communication with various devices using various means. In one particular embodiment, the network interface is bifurcated into a first network interface 406 for communicating with other server apparatuses and a second network interface 408 for communicating with a client device. Other implementations may combine these functionalities into a single network interface, the foregoing being purely illustrative.

In one exemplary embodiment, the first network interface 406 is a wide area network port that allows for communications with remote computers over the Internet (e.g., external databases). The first network interface 406 may further include a local area network port that enables communication with any of various local computers housed in the same or nearby facility. In at least one embodiment, the local area network port is equipped with a Wi-Fi transceiver or other wireless communications device. Accordingly, it will be appreciated that communications with the server 400 may occur via wired communications or via the wireless communications. Communications may be accomplished using any of various known communications protocols.

In one exemplary embodiment, the second network interface 408 is a network port that allows for communications with a community of personal devices. The second network interface 408 may be configured to interface to a variety of different networking technologies consistent with consumer electronics. For example, the network port may communicate with a Wi-Fi network, cellular network, and/or Bluetooth devices.

In one exemplary embodiment, the server 400 is specifically configured to provide managed workouts via exercise specific user interfaces in accordance with the principles described above. In particular, the illustrated server apparatus 400 stores one or more computer-readable instructions that when executed e.g., generates a workout and one or more associated exercises, provides the workouts and its one or more associated exercises for workout tracking, and obtains completion metrics for the one or more associated exercises.

FIG. 4B is a logical block diagram of one exemplary client device 450, useful in accordance with the various principles described herein. In one embodiment, the client device 450 includes a processor 452, non-transitory computer-readable medium 454, a first network interface 456, a user interface 458, and one or more sensors.

The components of the exemplary client device 450 are typically provided in a consumer electronics personal device such as a laptop, smart phone, etc. In some cases, the components of the exemplary client device 450 may be provided in a wearable form factor that is configured for everyday use and/or ruggedization. Examples of wearables include e.g., smart watches, smart shoes, pedometers, headphones, smart clothing, smart jewelry, smart glasses (and other head mounted displays), implantable devices, etc. It is appreciated that the embodiment of the client device 450 shown in FIG. 4B is only one exemplary embodiment of a client device 450 for the health and fitness system. As such, the exemplary embodiment of the client device 450 described herein with reference to FIG. 4B is merely representative of any of various manners or configurations of personal devices that are operative in the manner set forth herein.

The processing circuitry/logic 452 of the client device 450 is operative, configured, and/or adapted to operate the client device 450 including the features, functionality, characteristics and/or the like as described herein. To this end, the processing circuit 612 is operably connected to all of the elements of the client device 450 described below.

The processing circuitry/logic 452 of the client device 450 is typically controlled by the program instructions contained within the memory 454. The program instructions 454 enable control of a workout and logging of exercise metrics via an exercise specific user interface, as described in further detail supra. The client-side application at the client device 450 is configured to communicate with and exchange data with a host-side application at the health and fitness system as well as any number of other personal devices. In addition to storing the instructions, the memory 454 may also store data for use by the client-side application. As previously described, the data may include the workout data records, exercise data records, and completion data records, etc.

In one exemplary embodiment, the client device 450 is specifically configured to control a workout and log exercise metrics via an exercise specific user interface in accordance with the principles described above. In particular, the illustrated client device 450 stores one or more computer-readable instructions that when executed e.g., obtains a workout and its one or more associated exercises, displays each exercise and logs completion metrics, and stores and/or transmits the completion metrics for one or more associated exercises.

The network interfaces of the client device 450 allow for communication with various devices using various means. In one particular embodiment, the first network interface 456 enables communications with the health and fitness system and/or nearby peer devices. Other implementations may combine these functionalities into a single network interface, the foregoing being purely illustrative.

In one exemplary embodiment, the first network interface 456 is a local area network port that allows for communications with computers over an Ethernet connection (e.g., the health and fitness server 400). In another embodiment, the first network interface 456 is a cellular network port that allows for communications with a base station (that operates as a gateway to the broader Internet). In still other embodiments, the first network interface 456 may be configured to interface to a variety of different networking technologies consistent with consumer electronics. For example, the network port may communicate with a Wi-Fi network, cellular network, and/or Bluetooth devices. Communications may be accomplished using any of various known communications protocols.

In one exemplary embodiment, the user interface 458 is the interface that allows for communication between the user and the device. Common examples of human-machine input devices include elements such as e.g., touch screens, microphones, speakers, keypads, mice, buttons, and/or any number of other human input devices. In some variants, the user interface 458 may allow for unobtrusive communication between the user and the device via e.g., tactile, haptic, auditory, and/or time-insensitive visual interfaces. Common examples of such human-machine input devices include elements such as e.g., touch screens, microphones, speakers, buttons, rumble boxes, vibrators, and/or any number of other human input devices.

As used herein, the term "workout" refers to one or more activities performed by the user with measurable physiological and/or psychological impact. Examples of measurable physiological impacts may include without limitation e.g., cardiovascular strain, heart rate, caloric consumption, muscular exertion, fatigue, blood oxygenation, lactate production, blood occlusion, nervous system activation, temperature increase, sweat production, changes to form/body positioning (via video analysis), audible data (exhalations, foot strikes, etc.), and/or any other physical effect of exertion. Physiological data may be collected via one or more sensors 460 and/or the user device interface (e.g., buttons, touch screen, microphones, etc.) Common examples of sensors 460 include e.g., accelerometers, pedometers, magnetometers, heart rate monitors, blood sensors, microphones, cameras, and/or any other apparatus for collecting physiological data.

As used herein, "performance" and "performance metrics" refer to any set of workouts and/or predicted/expected physiological and/or psychological impacts for similar users based on e.g., physiology, psychology, fitness goals and/or any other relevant parameters. As used herein, the term "performance progression" is used to refer to a user's tolerable physiological and/or psychological impact as a function of time. For example, a user's physiological progression may be measured as a function of e.g., changes to heart rate as a function of distance run over multiple workouts, changes to maximum repetitions/sets of a load over multiple workouts, etc. Notably, while performance progression is generally measured physiologically, psychological measures may also have significant value. For example, some users may subjectively enjoy working out regardless of whether or not they improve their physiological performance. Also, a user's psychological impact may cause changes to motivation and/or outlook when they hit a physiological "plateau."

The above described system and method solves a technological problem common in industry practice related to workout navigation during physical exertion in common fitness environments. The above-described system and method improves the functioning of the computer/device by enabling users to focus on their physical exertion, rather than navigating a user interface.

Portions of the system and methods described herein may be implemented using one or more programs or suitable software code, such as the workout application on the client device and the health and fitness program on the server, both described above, each of which may reside within the memory of the respective computing devices as software or firmware. Such programs and code may be stored in the memory and executed by the processor of the display device or a system server or other computer in communication with the display device. A computer program product implementing an embodiment disclosed herein may therefore include one or more computer-readable storage media storing computer instructions translatable by processing circuitry/logic, a CPU, or other data processing device to provide an embodiment of a system or perform an embodiment of a method disclosed herein. Computer instructions may be provided by lines of code in any of various languages as will be recognized by those of ordinary skill in the art.

A "computer-readable medium" may be any type of data storage medium that can store computer instructions and/or data, including, read-only memory (ROM), random access memory (RAM), hard disks (HD), data cartridges, data backup magnetic tapes, floppy diskettes, flash memory, optical data storage, CD-ROMs, or the like. The computer-readable medium can be, by way of example, only but not by limitation, an electronic, magnetic, optical, electromagnetic, infrared, or semiconductor system, apparatus, system, device, or computer memory. The computer-readable medium may include multiple computer-readable media storing computer executable instructions, such as in a distributed system or instructions stored across an array. A "non-transient computer-readable medium" may be any type of data storage medium that can store computer instructions, including, but not limited to the memory devices discussed above.

In the foregoing description, various operations may be described as multiple discrete actions or operations in turn, in a manner that may be helpful in understanding the claimed subject matter. However, the order of description should not be construed as to imply that these operations are necessarily order dependent. In particular, these operations may not be performed in the order of presentation. Operations described may be performed in a different order than the described embodiment. Various additional operations may be performed and/or described operations may be omitted in additional embodiments.

It will be apparent to those skilled in the art that various modifications and variations can be made in the disclosed embodiments of the disclosed device and associated methods without departing from the spirit or scope of the disclosure. Thus, it is intended that the present disclosure covers the modifications and variations of the embodiments disclosed above provided that the modifications and variations come within the scope of any claims and their equivalents.

What is claimed is:

1. A user apparatus, comprising:
   a user interface;
   a network interface;
   a processor; and
   a non transitory computer-readable medium comprising one or more instructions, which when executed by the processor, causes the user apparatus to:
   obtain a workout comprising a plurality of exercises, wherein each of the plurality of exercises includes a prescribed completion value;
   for each exercise of the plurality of exercises:
      display an exercise specific user interface element based on the prescribed completion value, the exercise specific user interface element including:
         (i) the prescribed completion value for the exercise,
         (ii) a first option to amend the prescribed completion value or add an additional completion value for the exercise;
         (iii) a second option to skip the exercise; and
         (iv) a third option to move to a next exercise of the plurality of exercises;
      in response to selection of the first option, display a detailed exercise specific user interface element configured to receive an amended prescribed completion value or the additional completion value;
      in response to selection of the third option, log an actual completion value for the exercise based on the prescribed completion value and/or the completion value and transmit the actual competition value to a fitness server; and
      in response to selection of the second option, omit to log a completion value for the exercise.

2. The user apparatus of claim 1, wherein the prescribed completion value comprises a duration; and
   where the exercise specific user interface element comprises a timer set to the duration.

3. The user apparatus of claim 1, wherein the prescribed completion value comprises a number of repetitions; and
   where the exercise specific user interface element comprises a counter set to the number of repetitions.

4. The user apparatus of claim 1, wherein the prescribed completion value comprises a distance; and
   where the exercise specific user interface element comprises a distance tracker set to the distance.

5. The user apparatus of claim 1, wherein another exercise of the plurality of exercises includes another prescribed completion value; and
   wherein the one or more instructions, when executed by the processor, causes the user apparatus to display another exercise specific user interface element based on the another prescribed completion value.

6. The user apparatus of claim 1, wherein the exercise specific user interface element causes the prescribed completion value to be logged as the actual completion value.

7. The user apparatus of claim 1, wherein the user apparatus further comprises a sensor; and
   wherein the one or more instructions, when executed by the processor, causes the user apparatus to sense the actual completion value.

8. A user apparatus, comprising:
   a user interface;
   a network interface;
   a processor; and
   a non transitory computer-readable medium comprising one or more instructions, which when executed by the processor, causes the user apparatus to:
   obtain a workout comprising a plurality of exercises, wherein the plurality of exercises has a prescribed sequence;
   for each exercise of the plurality of exercises:
      display a first exercise specific user interface element for the at least one exercise the exercise specific user interface element including:

(i) a prescribed completion value for the exercise,
(ii) a first option to amend the prescribed completion value or add an additional completion value for the exercise;
(iii) a second option to skip the exercise; and
(iv) a third option to move to a next exercise of the plurality of exercises; and
responsive to selection of the second option or the third option, transition to a next exercise of the workout based on the prescribed sequence;
responsive to selection of the third option transmit a completion value for the at least one exercise to a fitness server.

9. The user apparatus of claim 8, wherein the one or more instructions, when executed by the processor, causes the user apparatus to display a second exercise specific user interface element for the next exercise of the workout; and
wherein first exercise specific user interface element differs from the second exercise specific user interface element.

10. The user apparatus of claim 8, wherein the workout further comprises at least one alternate exercise.

11. The user apparatus of claim 10, wherein the one or more instructions, when executed by the processor, causes the user apparatus to: responsive to a user input, transition to the at least one alternate exercise.

12. The user apparatus of claim 8, wherein the workout further comprises an alternate plurality of exercises.

13. The user apparatus of claim 12, wherein the one or more instructions, when executed by the processor, causes the user apparatus to transition to the alternate plurality of exercises based on the completion value for the at least one exercise.

14. The user apparatus of claim 8, wherein the one or more instructions, when executed by the processor, causes the user apparatus to: responsive to a user input, modify the prescribed sequence.

15. A method for controlling a workout and logging of exercise metrics, comprising:
obtaining the workout comprising an exercise;
displaying an exercise specific user interface element based on a prescribed completion value associated with the exercise, the user interface element including:
(i) the prescribed completion value for the exercise,
(ii) a first option to amend the prescribed completion value or add an additional completion value for the exercise;
(iii) a second option to skip the exercise; and
(iv) a third option to move to a next exercise of the workout;
following selection of the second option or the third option, displaying an additional exercise specific user interface element association with a subsequent exercise of the workout;
following selection of the third option, logging an actual completion metric for the exercise; and
following selection of the third option, providing the actual completion metric to a fitness server.

16. The method of claim 15, wherein the prescribed value comprises a modality of exercise measurement.

17. The method of claim 15, wherein the prescribed value comprises a prescribed sequence.

18. The method of claim 15, wherein the prescribed value comprises a prescribed completion value.

19. The method of claim 18, further comprising pre-populating the exercise specific user interface element based on the prescribed completion value.

20. The method of claim 18, further comprising logging the prescribed completion value as the actual completion metric.

* * * * *